United States Patent [19]
Widmer et al.

[11] Patent Number: 6,110,727
[45] Date of Patent: Aug. 29, 2000

[54] METHOD AND APPARATUS FOR BIOLOGICAL TREATMENT OF ORGANIC MATERIALS

[75] Inventors: Christian Widmer, Homburgerstrasse 47, 4052 Basel, Switzerland; Wolfgang Stehle, Schlier, Germany; Artur Wellinger, Guntershausen, Switzerland

[73] Assignee: Christian Widmer, Basel, Switzerland

[21] Appl. No.: 09/117,335

[22] PCT Filed: Jan. 24, 1997

[86] PCT No.: PCT/EP97/00341

§ 371 Date: Jul. 27, 1998

§ 102(e) Date: Jul. 27, 1998

[87] PCT Pub. No.: WO97/27158

PCT Pub. Date: Jul. 31, 1997

[30] Foreign Application Priority Data

Jan. 25, 1996 [DE] Germany .......................... 196 02 489

[51] Int. Cl.$^7$ .................................. C05F 9/02; C05F 9/04
[52] U.S. Cl. .................. 435/262; 435/290.2; 435/290.4; 71/9; 210/603
[58] Field of Search ................................ 435/262, 290.1, 435/290.2, 290.3, 290.4; 71/9; 210/603

[56] References Cited

U.S. PATENT DOCUMENTS

| | | |
|---|---|---|
| 4,758,344 | 7/1988 | Wildenauer . |
| 5,288,399 | 2/1994 | Schulz . |
| 5,534,437 | 7/1996 | Arrau . |
| 5,846,815 | 12/1998 | Wright . |

FOREIGN PATENT DOCUMENTS

| | | |
|---|---|---|
| 0037612 | 7/1985 | European Pat. Off. . |
| 0567184A1 | 10/1993 | European Pat. Off. . |
| 4343767C1 | 2/1995 | Germany . |
| 4423099A1 | 3/1995 | Germany . |
| WO 95/20554 | 8/1995 | WIPO . |

OTHER PUBLICATIONS

Bergmann/Schäfer: Lehrbuch der Experimentalphysik [Textbook on Experimental Physics], vol. 6, 1992, pp. 452 et seq.

*Primary Examiner*—William H. Beisner
*Attorney, Agent, or Firm*—Venable; George H. Spencer; Robert Kinberg

[57] ABSTRACT

A process and an apparatus for carrying out the process for the biological treatment of organic wastes. In order to achieve more effective treatment of the material, in a horizontally oriented reactor, a circulating agitator is disposed which causes circulation of the material with simultaneous advance. The material is leached via spray arms, with simultaneous intense aeration of the material to generate an aerobic biological degradation process.

21 Claims, 2 Drawing Sheets

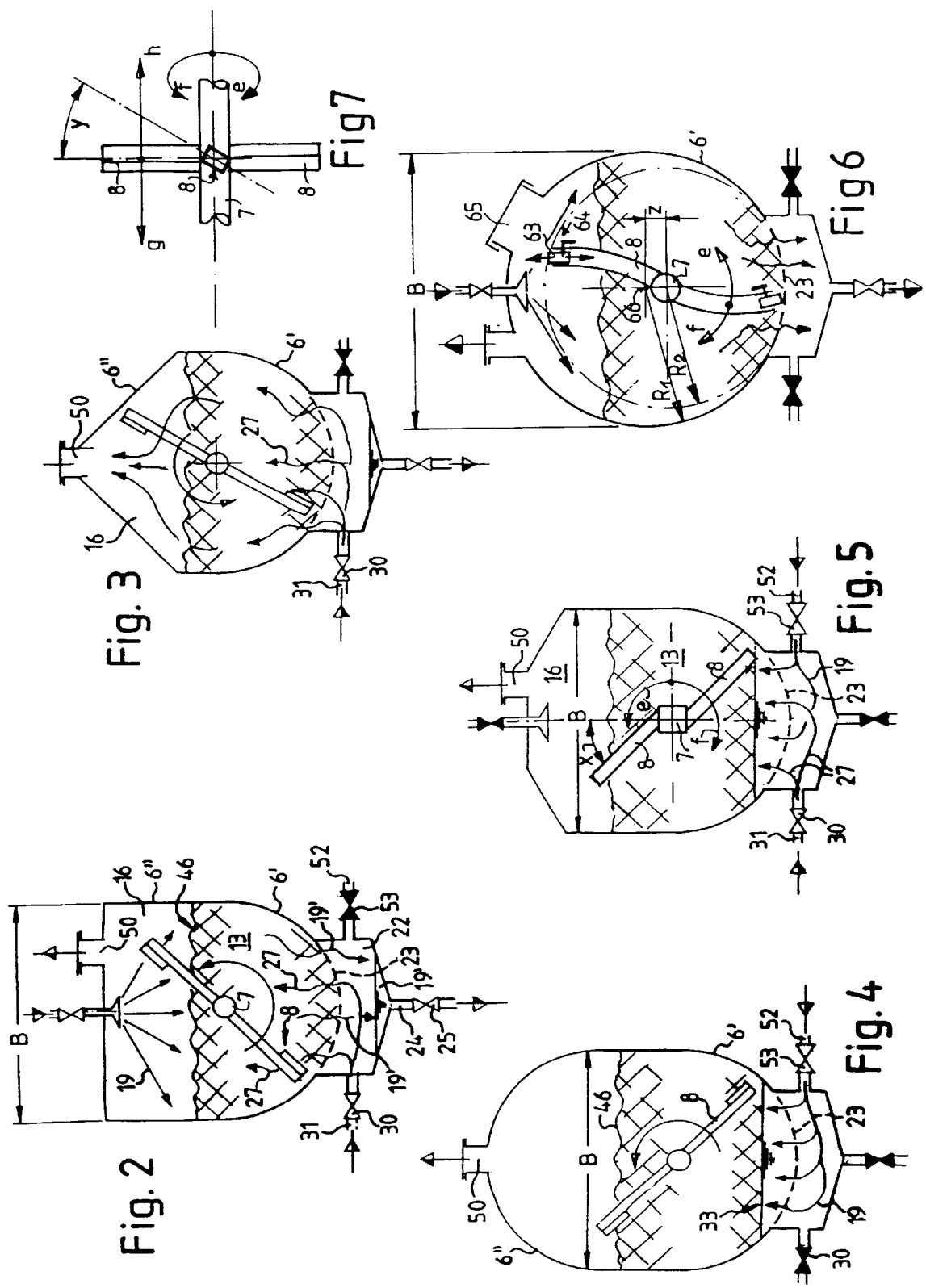

METHOD AND APPARATUS FOR BIOLOGICAL TREATMENT OF ORGANIC MATERIALS

BACKGROUND OF THE INVENTION

1. Filed of the Invention

The invention relates to a process for the biological treatment of organic materials. The invention equally relates to an associated apparatus for carrying out the process.

2. Description of the Related Art

The waste industry has been subjected for some years to an accelerated restructuring process. In this process, the problem of disposal and utilization of biological wastes from households, commerce and industry is also increasingly assuming prominence. Numerous processes have been disclosed for biological, mechanical/biological or chemical/biological residual waste utilization. The best-known process used is composting animal and plant wastes, the organic substances being substantially degraded or converted by micro-organisms in an aerobic conversion process. In addition to the aerobic rotting process, anaerobic fermentation for treating biological wastes has also been disclosed, which likewise decomposes refuse with the action of microorganisms, with the exclusion of air. The two processes are used in waste technology either individually or in combination.

In particular during composting using an aerobic treatment, in a known preliminary rotting process, the material, to mix it, is continuously agitated in a rotting drum and is converted to fresh compost in a period of approximately one to two days. In the case of a static preliminary rotting, the material to be composted is at rest, and is aerated during this. This requires a considerable amount of space, in particular for the subsequent secondary rotting operation as well. The advantage of the dynamic preliminary rotting with continuous mixing of the refuse mixture is good aeration of the material, the occurrence of anaerobic points in the material being prevented.

The anaerobic treatment of organic refuse wastes or biowastes which has likewise been disclosed in recent years is based on an anaerobic fermentation, i.e. on a digestion process, which, with the exclusion of air, leads to biogas production in a weakly exothermic reaction. A process of this type has been disclosed, for example, by European Patent Document No. EP 0 037 612 B1, in which organic wastes are treated in a static process in a reactor with a leaching liquid which leaches soluble inorganic and/or organic materials from the material to be treated. This process takes place with the exclusion of air, i.e. under anaerobic conditions, as a so-called hydrolysis.

A disadvantage of this known process is, owing to the static disposition of the material, the formation of bypass flow channels, i.e. the applied liquid seeks the path of least resistance, via isolated channels, owing to a type of chimney effect, so that the material is only incompletely irrigated with washing liquid. The result is dead zones which are not leached, or are leached only insufficiently.

SUMMARY OF THE INVENTION

The object underlying the invention is to propose an improved process for the biological treatment, in particular, of wet organic materials (biorefuse), in which said disadvantages do not occur and which represents, in particular, an extremely effective and inexpensive treatment method for such materials. The central concept underlying the invention here is that a combined treatment of the material in the form of a leaching process and a targeted aerobic material treatment leads to a very highly effective rotting of the product. In this process, the invention makes use of individual process steps, some of which are known per se, which in combination, however, lead to an effective treatment of the biorefuse.

The process according to the invention has the advantage, in particular, that on account of a dynamic treatment of the material, short-circuit flow channels are prevented or destroyed both in the vertical and in the horizontal direction in the material, so that the irrigation carried out with leaching liquid covers the material uniformly and in all places, so that no dead zones form. The organic mass is continuously or discontinuously circulated and simultaneously subjected to an aerobic decomposition of material. In the course of this, irrigation is carried out from top to bottom, with periodic simultaneous exposure to an airstream from bottom to top to achieve aerobic degradation.

The rotting process is carried out in a reactor constructed according to the invention having an appropriate circulation device for the material and an irrigation system and means for feeding fresh air and removing the leaching liquid.

It is particularly advantageous to operate the reactor in a through-flow mode, i.e. the reactor is charged from one side with material which is slowly transported through the reactor owing to the circulation mechanism. On the other side, the material is accordingly taken out of the reactor.

A flow-through mode of this type has the advantage, in particular, that different material properties exist over the length of the reactor, since, owing to the residence time of several days, the degree of degradation of the material changes over the length of the reactor and the material can accordingly be subjected to a different treatment. As a result, treatments differing in space and time, in particular over the length of the reactor, are carried out both with leaching liquid and with fresh air for the aerobic rotting.

The reactor according to the invention therefore makes possible extremely flexible handling of the material to be introduced, depending on its composition and, in particular, depending on organic loading, temperature and water content, the aerobic conversion of the material is able to be measured over the length of the reactor and the process is able to be under closed-loop or open-loop control.

The degree of filling of the reactor with the material to be treated and its three-dimensional shaping and the irrigation of the surface of the material are advantageously matched to one another in such a manner that the maximum possible material surface area is uniformly irrigated, so that no dead zones are formed.

It is further advantageous that, in the lower area of the reactor, a plurality of chambers are provided which equally serve for feeding fresh air and/or as an outlet for the leaching liquid, the chambers being covered in particular by a screen filter to avoid as far as possible passage of material. The covering screen can be cleaned by backflushing, a plurality of chambers being able to interact.

It can also be advantageous to flood the lower area of the reactor with leaching liquid in order to produce a type of flotation of the material for better circulation, which is preferably expedient in the case of very tough and/or very dry material.

The process according to the invention is preferably further developed by the fact that various mechanical/biological stages are arranged downstream of the through-flow reactor, which stages purify and regenerate the leaching liquid and free this from the high organic loading by an anaerobic treatment. A leaching liquid treated in this manner can be recirculated back to the reactor according to the invention.

BRIEF DESCRIPTION OF THE DRAWINGS

Advantages with respect to the apparatus according to the invention for carrying out the process are specified in more detail in the description of an exemplary embodiment below, wherein:

FIGS. 2 to 6 show a longitudinal section through the reactor having a chamber situated at the bottom in various operating states, and FIG. 7 shows a detail of the longitudinal view of the agitator shaft.

DETAILED DESCRIPTION OF THE PREFERRED EMBODIMENTS

Figure 1:
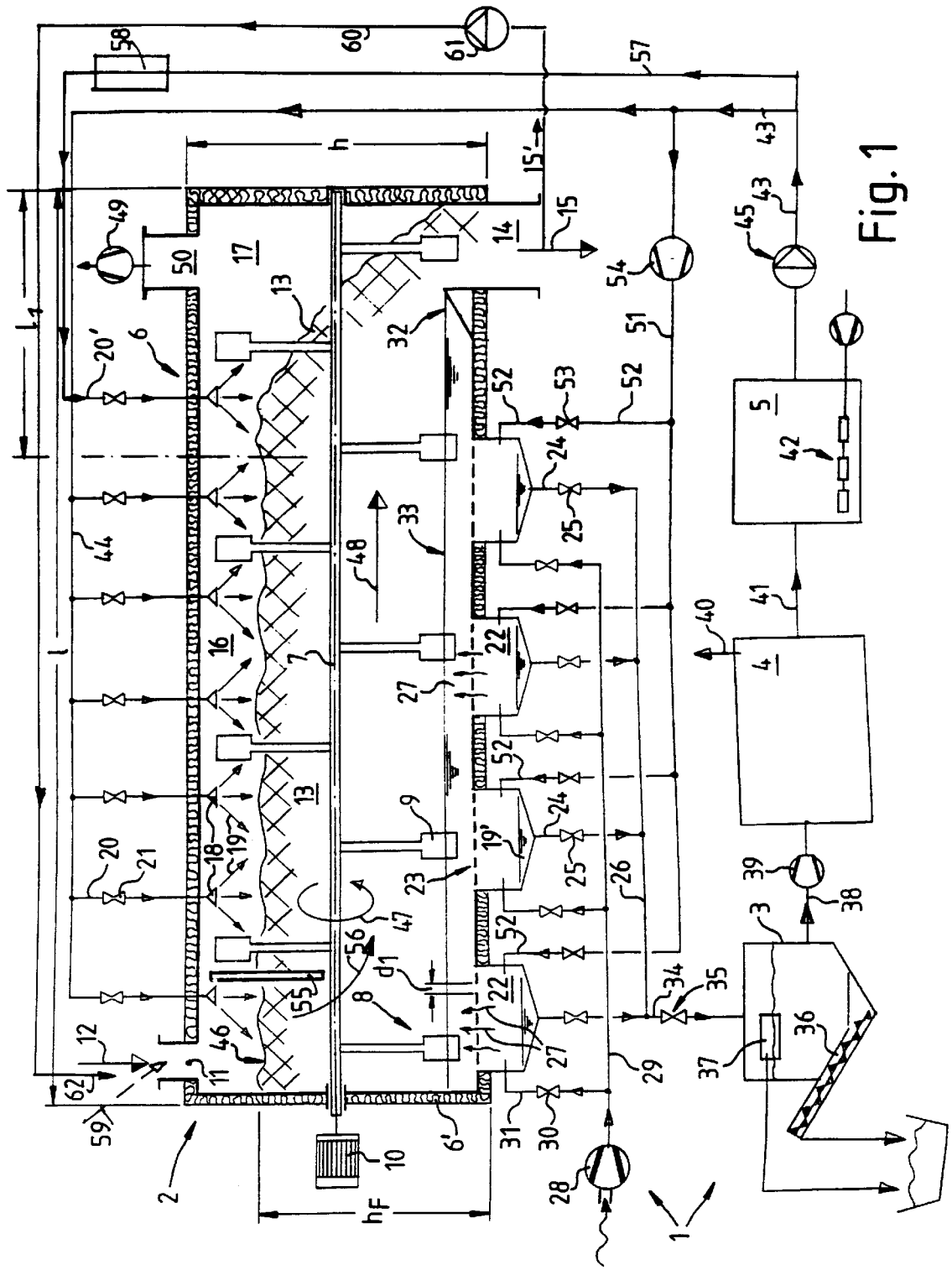
FIG. 1 shows a side view of a reactor according to the invention for treating the biorefuse having downstream stages in a diagrammatic representation for treatment of the leaching liquid.

The schematic diagram shown in FIG. 1 shows a plant 1 for the biological treatment of preferably wet biorefuse having a plurality of components, consisting of a solids reactor 2 for treating the organic material and, connected downstream of the reactor 2, processing stages 3 to 5 for after-treatment and reprocessing of the reusable leaching liquid.

The reactor 2, in accordance with the drawing in FIG. 1, consists of an elongate housing 6 having a vertical cross section as shown in FIGS. 2 to 5. The length 1 of the housing can differ very greatly, depending on the size of the plant, and, completely by way of example, 1 can be 20 to 30 meters. The height h of the reactor compartment is in this case 4 to 5 meters. In the lower area, the cross section of the reactor housing 6' is roughly cylindrical, and in the upper area 6", rather, is rectangular (FIG. 2), triangular (FIG. 3) or, overall, oval (FIG. 4). Through the reactor housing 6 passes a horizontal shaft 7, which is preferably constructed as a spined agitator 8 having paddle- or blade-shaped circulation elements 9. The shaft 7 is driven via a drive motor 10.

According to the drawing in FIG. 1, the housing 6 of the reactor 2 has at its one end, at the top left in the figure, a filling port 11 through which the reactor is charged with an organically loaded material 13 in accordance with the arrow 12. This is in particular wet organic materials or biomasses which originate in particular from biological wastes from households, from the food-processing industry, agriculture, or from an organic fraction of the residual refuse (landfill refuse) or the like (biorefuse). Materials having the most varied compositions both with respect to organic loading and with respect to degree of moisture and initial temperature can be used.

At the other end of the reactor 2, in accordance with the drawing in FIG. 1, at the lower right end, there is situated an outlet port 14 for the material 13 after treatment has been carried out, which material is discharged from the reactor in accordance with arrow 15.

The reactor 2 shown in FIG. 1 is filled in its interior 17 up to a mean filling height $h_F$ with material 13, so that an overlying air space 16 is established. The filling height of the material can be, for example, two thirds of the overall height h.

In the upper area of the reactor interior 17, there are situated a multiplicity of spray arms 18 for subjecting the material 13 to a leaching liquid 19 which exits from the spray arms 18 in accordance with an arrow representation. An upper feed line 20 having a control valve 21 leads the leaching liquid 19 to the individual spray arms 18. In the exemplary embodiment according to FIG. 1, for example, seven spray arms 18 are arranged distributed over the length of the reactor interior.

In the lower area of the reactor 2, in the exemplary embodiment according to FIG. 1, a plurality of chambers 22, and in particular four chambers 22, are arranged adjacently which are separated from the interior 17 of the reactor by means of a covering screen 23, so that the material 13 does not, as far as possible, fall into the chamber 22. The screen hole diameter is between 6 and 12 mm and is, in particular, 8 mm in diameter. This diameter is symbolized by $d_1$.

The chamber 22 has a double function. Firstly, it serves to collect the leaching liquid which passes through the material 13. This leaching liquid is designated 19' in the chamber 22 and is led to a manifold 26 via an outlet line 24 having a valve arrangement 25.

In addition, the chamber 22 serves to treat the material 13 with fresh air 27, as is shown symbolically by arrows in FIG. 1. The fresh air is fed via a compressor 28 to a manifold 29, and from there is fed via control valves 30 via the line 31 to the respective chamber 22.

On account of the possibility provided for backflushing and flooding the reactor interior 17 with leaching liquid from the chambers 22, an overflow wall 32 or overflow edge is provided in the area of the outlet port 14. The associated upper liquid level 33 is shown symbolically.

The lower manifold 26 for the leaching liquid removed from the chambers leads via a shared line 34 having a valve arrangement 35 to the downstream processing stages 3 to 5 for treating the leaching liquid. These treatment stages comprise, in particular, firstly an interference separator 3 which serves to separate off sink material of all types, such as, for example, sand, stones or the like, i.e. all substances which pass through the screen 23 as sink material. Sedimenting materials are removed via a conveyor device 36, float materials or suspended materials such as plastic, wood or the like are removed from the interference separator via a skimmer device 37.

The leaching liquid thus purified in the interference separator 3 is led via a line 38 by pump 39 to a downstream anaerobic reactor stage 4 which is constructed, for example, as a methane reactor. In this methane reactor, the organics-enriched leaching liquid is degraded and purified by methane bacteria, biogas or methane gas 40 being formed as metabolic product.

Finally, the downstream treatment stage comprises a further aerobic purification reactor 5 which, via a line 41, converts the anaerobic state of the leaching liquid into an aerobic state, an aerator 42 ensuring an aerobic decomposition and activation of the leaching liquid.

Conventional components and plant sections according to the known process diagram can be used for these three downstream treatment stages 3 to 5 for the leaching liquid.

The leaching liquid, which has been thus treated and purified and, in particular, freed from high organic loading, is taken off from the aerobic purification stage 5 via a line 43 and fed to a manifold 44 by a pump 45. This manifold 44 leads to the individual feed lines 20 to the spray arms 18.

A leaching liquid treated in this manner consists, after a defined start-up phase of the plant 1, of a slightly acidified liquid, the acidification of the pure water initially used as leaching liquid taking place owing to the aerobic treatment of the material 13 in the reactor 2. This process corresponds to a hydrolysis, i.e. to a dissolution of soluble salts with acidification of the water.

The plant and, in particular, the solids reactor 2 act as follows:

The material 13 which is fed continuously or discontinuously to the inlet port 11 of the reactor 2 generally consists of a wet organic material, in particular biorefuse, as mentioned at the outset. The filling height of the material 13 is approximately $h_F \approx 2/3$ of the internal height h, so that an upper air space 16 is formed. In this case, in accordance with the depiction in FIGS. 2 to 5, the filling height $h_F$ is dimensioned such that virtually the entire width B of the surface 46 of the material 13 can be sprayed with leaching liquid 19. For this reason, the upper area of the reactor, to avoid reduction in the material surface area at a corresponding filling height, is constructed to be rectangular (FIG. 2), triangular (FIG. 3) or, overall, oval (FIG. 4) in cross section.

The uniform spraying of the material 13 with the slightly acidified liquid 19 by the spray arms 18 causes a leaching of soluble organic and/or inorganic substances and/or water-soluble fatty acids which are formed by decomposition of the material 13. It is of importance here that the material 13 is continually and continuously or discontinuously circulated by a type of spined agitator 8 having paddle-shaped or blade-shaped circulation elements 9, in order firstly to obtain good mixing of the material 13. However, the circulation also serves, in particular, for avoiding so-called vertical and horizontal bypass flow channels, which would form in the material 13 owing to the liquid stream of the leaching liquid, so that nonuniform wetting or leaching, and thus dead zones, would form. The paddle-shaped or blade-shaped agitator arms 9 can, in accordance with the drawing in FIG. 1, be arranged in a multiplicity next to and/or opposite one another, the paddle-shaped end blades 9 being able to lie adjacently or overlapping, so that a type of disk-shaped circulation of the material occurs. On account of the rotary motion of the shaft 7 (arrow 47), in addition, slow longitudinal transport in the direction of the arrow 48 through the reactor interior 17 takes place, so that the material 13 migrates slowly through the reactor and finally, after a residence time of, for example, 4 to 8 days, leaves the reactor interior 17 through the outlet port 14.

During this treatment procedure and, in particular, simultaneously or intermittently to the leaching process, fresh air 27 is supplied in a specific manner via the lower chambers 22 to the material 13, which leads to a simultaneous aerobic treatment of the material together with an exothermic self-heating of the material. This aerobic treatment is completed with a microbiological degradation of the organic substances by appropriate microorganisms, the intensive odor development being encapsulated on account of the closed construction of the reactor. The upper air space 16 of the reactor above the material 13 is continually exhausted by a suction pump 49 via an air outlet orifice 50, so that adequate aeration of the upper air space 16 also occurs. The targeted extraction of the upper air by means of reduced pressure ensures that only aerobic conditions are present in the upper air space 16 as well.

On account of the continuous or discontinuous flow of the material 13 over the longitudinal direction of the reactor, highly different material compositions are situated within the reactor as a result of the different residence time. For example, relatively fresh and untreated material is situated in the area of the filling port 11, whereas in the area of the rear outlet port 14 the material has already been treated for, for example, between 4 and 8 days. Accordingly, over its length 1, the reactor can comprise highly different treatment stages which can vary greatly.

Measuring devices, which are not shown in more detail, for determining the most varied parameters of the material, such as its composition, its temperature, the moisture content etc., are assigned to the reactor, further measured data being available on the leaching liquid and the feed air. Depending on the progress of the treatment, the adjacently arranged spray arms 18 can then receive different flow rates of leaching liquid, in order to obtain varying leaching of the material composition present beneath each one. Equally, the, for example four, chambers 22 lying beneath can receive different flow rates of fresh air 27, in order to influence the aerobic decomposition process of the material 13. Correspondingly, the mixing of the material which is carried out can additionally affect the material properties. For example, in the case of an aerobic degradation of the material, a certain increase in the surface area of the organic material takes place, which at the same time would promote the process of leaching by the leaching liquid 19. Therefore, depending on the degree of aerobic degradation carried out, the optimum amount of leaching liquid must be added here, which can be determined by experiment. Furthermore, for example, increasing the temperature of the leaching liquid, owing to the aerobic decomposition of the material, has a beneficial effect on the subsequent treatment stages 3 to 5, in order to obtain optimum regeneration of the leaching liquid. A preferred treatment of the material in the starting area and in the final area of the reactor is described in claims 3 and 4.

The interior 17 of the reactor 2 can therefore be monitored by means of appropriate measuring devices and the progress of the process can be controlled by a preset program or else as a function of the measured values.

The adjacent lower chambers 22 are closed by the covering screens 23 in such a manner that the material 13 as far as possible cannot pass into the chamber 22. A critical factor for this is the mesh width having the diameter $d_1$.

However, from time to time the screen 23 must be cleaned of impurities or blockages, which is performed by a back-flush operation. For this purpose, the liquid 19' present and collected in the chamber 22 is either backed up by closing the valves 25, so that the liquid rises within the chamber 22, or purified leaching liquid is taken off from the line 43, 44 via a manifold 51 and specifically fed to the chamber 22 via feed lines 52 having a valve arrangement 53 (see FIGS. 4, 5). The liquid can be backed up here up to an upper liquid level 33 corresponding to the height of the overflow wall 32. By a possible additional impingement of this liquid compartment with compressed air via the compressor 28, the respective impinged screen 23 can be blown free and thus cleaned. This operation is also supported, in particular, by means of the liquid pump 45 or a further pump 54 in the manifold 51.

The covering screen 23 cleaning operation can also be carried out in such a manner that in each case only one chamber or only certain chambers are subjected to a back-flushing operation and the backflushing liquid ascending as a result is removed in the adjacent, or one of the adjacent, chambers. Thus, for example, the first and third chamber 22 in FIG. 1 can each be drained into the adjacent chamber during the backflushing operation.

Backing up the liquid, for example, up to a liquid level 33 can, furthermore, also have the effect that the material 13 floats on this liquid cushion and this material can be more readily mixed, in particular, in the case of tough or very dry material.

As mentioned above, the material 13 can have highly variable treatment with leaching liquid 19 and fresh air 27 with simultaneous or intermittent circulation of the material. For example, approximately 0.5–2 m³ of leaching liquid per day and per metric ton of material are converted in the reactor. The operating time of the agitator can be between 5 and 60 min per hour, at a speed of 1 to 2 rpm.

FIG. 2 shows, as an example, irrigation of the material over as far as possible all of the upper surface 46 over its maximum possible width with simultaneous circulation of the material by means of the spine agitator 8. The leaching liquid 19 uniformly passing through the material is collected in the lower area of the chamber 22 as liquid 19'. In this state, there is an additional exposure to fresh air 27, so that the aerobic decomposition process of the material 13 takes place simultaneously.

In the usual state, the leaching process and the fresh air feed take place simultaneously. FIG. 3 shows fresh air feed 27 alone without the leaching operation.

FIG. 4 shows the backflush operation up to a depth of liquid having a liquid level 33 as described above. As a result, the material floats on this liquid cushion, so that the circulating agitator 8 can carry out mixing more readily. A slight elevation of the material within the reactor is not harmful during this mixing operation.

The depiction of the arrangement in FIGS. 2, 3 shows the fresh air feed operation via the line 31 having valve arrangement 30 via the lower covering screen 23 to the material 13. The air serves for the aerobic degradation or the aerobic decomposition of the material by microorganisms, the air being collected in the upper air space 16 and extracted from the reactor interior 17 via the air outlet port 50.

FIG. 5 shows the back wash operation via the line 52 with valve 53 open, with simultaneous impingement by compressed air; FIG. 4 shows this operation without compressed-air impingement, i.e. valve 30 closed.

The process according to the invention and the associated apparatus can be still further optimized by the measures described below.

As shown in FIG. 1, an additional partition and submerged wall 55 is mounted in the area of the inlet port 11. This submerged wall 55 prevents the fresh material introduced from being able to pass unhindered on the material surface 46 from the entrance 11 in a pseudoshort circuit to the exit 14. The fresh material must rather initially pass through below the submerged wall 55 along the path indicated by the arrow 56 and cross the lower part of the reactor.

In special cases it can be expedient for the material treated in the reactor to be sanitized prior to exit from the solids reactor 2, i.e. for it to be subjected to a defined temperature for a defined time. This can be expediently carried out by the rear vessel content 13 being additionally heated on a defined section $1_1 \approx (\frac{1}{3} - \frac{1}{4})$ 1. For this purpose, for example, from line 43, via a parallel line 57, circulation water is taken off which is heated in a heat accumulator which is not shown in more detail, or is heated in a heat exchanger 58 which is shown diagrammatically. The circulation water of the line 57 can then be added in a targeted manner in the upper area of the reactor either to the manifold 44 or targeted impingement is carried out, e.g. via feed line 20 in the rear reactor area. This is shown diagrammatically in FIG. 1 via the last feed line 20'.

An expedient development of the process can also be continuous or discontinuous addition of activated sludge or excess sludge from an activation plant in the area of the filling port 11. The aerobic microorganisms introduced together with the activated sludge represent a reaction accelerator for the biological conversion of the organic materials. This addition is indicated diagrammatically by arrow 59. Microorganisms already adapted to the waste material have proved to be particularly advantageous in this case, which microorganisms can be taken off either from the aerobic percolate treatment stage or, for example, from a biological leachate water purification plant. The division of the material stream 15 into a substream 15', indicated in the area of the outlet port 14, also enables partial recycling via the line 60 of material treated in the percolator 6. An additional transport element 61 can support this operation. The partial recycling of material treated in the percolator 6 and of the microorganisms which are already adapted present therein can likewise accelerate the reaction. This is shown diagrammatically via the feed line 60 by arrow 62 in the area of the inlet port 11.

According to the depiction of the invention in FIGS. 2 to 4, the agitator 8 has corresponding stirrer arms or circulation elements which lead radially away from the drive shaft 7. According to the drawing in FIGS. 5 and 6, to support the stirring effect, the agitator 8 can also change its direction at intervals. In this case, the stirring effect can be reinforced by a blade-like twisting of the stirrer arms 8 or circulation elements being performed at a pitch angle x in accordance with FIG. 5 or else by a curved arrangement in accordance with the drawing in FIG. 6. In the case of a blade-shaped arrangement of the stirrer arms 8, the main direction of rotation is indicated by e. When the direction of rotation is in the direction of arrow e, optimum mixing is achieved. However, with material 13 which is highly fouled, for example with plastic films and strings, etc., these may become wound round the stirrer arms 8. In order to free the stirrer arms 8 from this fouling, the agitator shaft 7 is rotated at intervals in the opposite direction in accordance with arrow f, by which means, on account of the slightly inclined, tangential or curved arrangement of the stirrer arms 8, the fouling is scraped off from the stirrer arms 8 by the friction on the material 13 itself. The same effect is produced both in the drawing according to FIG. 5 and that according to FIG. 6.

According to the drawing as in to FIG. 6, in addition, the lower screen 23 can further be cleaned by means of the agitator. For this purpose, at the ends of the stirrer arms 8, an replaceable part 63 can be mounted as a slide. This replaceable part, or this scraper, 63 at the ends of the stirrer arm 8 can be introduced, adjusted or exchanged from the exterior via the additional port 65 by a clamping apparatus 64 not shown in more detail.

In the case of a vessel 6' in cylindrical arrangement according to FIG. 6, in addition, the agitator 8 can be displaced off-center, preferably downward, by a distance z from the longitudinal cylindrical axis 66. As a result of this arrangement, the agitator radius $R_2$ is less than the cylindrical vessel radius $R_1$, so that the scrapers 63 as a result only act on the lower screen 23 and do not cause undesired wear on the vessel inner wall.

According to the detail of the longitudinal view of the agitator shaft 7 shown in FIG. 7, the stirrer arms 8 can advantageously also be mounted on the shaft 7 twisted by an angle y. Such a twisting of the stirrer arms causes a blade effect similar to a ship's screw and thus an axial advance in parallel to the longitudinal axis of the agitator shaft 7. If, for example, the agitator shaft 7 is rotated in the direction of the arrow e, the material 13 is transported in the direction of flow g. If the direction of rotation is changed to accord with the arrow f, the material is shifted in the direction of the arrow h. The direction of rotation of the agitator shaft 7 can therefore cause a forward or backward thrust of the material by the stirrer arms twisted in the shape of a propeller.

With certain material compositions, this abovedescribed effect is required for back-mixing and inoculation of fresh material 12 with the reactor material 13.

The invention is not restricted to the exemplary embodiment shown and described. Rather, it also includes developments which can be made by those skilled in the art within the scope of the patent claims.

What is claimed is:

1. A process for biological treatment of organic waste material in a solids reactor, comprising the steps of:
    charging the reactor with the waste material at a first end of the reactor;
    feeding air to the waste material so the air flows through the waste material in a first direction, to cause an aerobic degradation of organic substances in the waste material, whereby the waste material heats to a process temperature in the reactor;
    applying leaching liquid to the material so the leaching liquid flows through the waste material in a second direction opposite to the first direction and so that at least one of soluble organic substances, soluble inorganic substances, and water soluble fatty acids are leached from the waste material into the leaching liquid;
    agitating, circulating and transporting the waste material with an agitating/circulating/transporting mechanism in the reactor to mix the waste material, prevent the formation of liquid bypass channels in the waste material, and transport the waste material towards a second end of the reactor; and
    removing the leaching liquid charged with at least one of soluble organic substances, soluble inorganic substances, and water soluble fatty acids at a lower part of the reactor.

2. The process as claimed in claim 1, wherein the material is transported in at least one of forward and backward directions through the reactor along its length, and wherein at least one of the steps of the application of leaching liquid and the feeding of air are selected to be carried out uniformly, or varying over the length of the reactor depending on the composition of the material.

3. The process as claimed in claim 2, wherein the applying step includes applying the leaching liquid uniformly and simultaneously with feeding of air, wherein aerobic degradation of the material causes heating of the material and the leaching liquid, and the heated leaching liquid causes leaching of at least one of soluble organic substances, soluble inorganic substances, and water soluble fatty acids.

4. The process as claimed in claim 1, wherein the second end has an outlet area having an outlet port for the material, the process further comprising at least one of the following steps to reduce water content of the material in the outlet area:
    reducing or shutting off application of leaching liquid; and
    increasing feeding of air; and
    wherein the process further comprises the step of:
    sanitizing the material in the outlet area by feeding a preheated backflow liquid during a predetermined time interval.

5. The process as claimed in claim 1, comprising the step of using at least one of open loop control and closed loop control to select between continuous and discontinuous circulation of the material depending on at least one of the organic loading, temperature, and water content of the material.

6. The process as claimed in claim 1, wherein the reactor has a free air space above the material that enables uniform application of leaching liquid to the upper surface of the material.

7. The process as claimed in claim 1, wherein the lower part of the reactor has at least two chambers which perform at least one of the functions of:
    feeding fresh air; and
    providing an outlet for leaching liquid,
    wherein the chambers are separated from the interior of the reactor by a screen to prevent entry of solids into the chambers.

8. The process as claimed in claim 7, further comprising the step of cleaning the screen by backflushing the reactor interior by flooding at least one of the two chambers with a backflush liquid and feeding the backflush liquid to an adjacent chamber.

9. The process as claimed in claim 8, wherein air is forced in a direction along the reactor interior during backflushing operation.

10. The process as claimed in claim 7, further comprising the step of flooding the reactor with leaching liquid via at least one of the two chambers so that the material floats on the liquid and the floating material is transported in at least one of forward and backward directions in the reactor.

11. The process as claimed in claim 1, wherein the agitating/circulating/transporting mechanism comprises a spined agitator having a horizontal shaft passing through the reactor interior and a stirring arm, wherein the material is processed in the form of a disk-shaped or plug-shaped advance of the material.

12. The process as claimed in claim 1, further comprising the steps of:
    taking the leaching liquid out of the reactor;
    feeding the leaching liquid to downstream treatment stages;
    subjecting the liquid to at least one of a mechanical treatment, an anaerobic treatment, and a following aerobic treatment, to purify the liquid for regeneration; and
    feeding the treated leaching liquid to back flush at least one of the chambers and the free space situated above the material in the reactor.

13. The process as claimed in claim 12, wherein the reactor has treatment stages comprising:
    an interference separator for separating sink materials and discharging floating suspended materials; and
    an anaerobic methane reactor for treating the leaching liquid, so that organic-enriched leaching liquid is degraded and purified by methane bacteria with the formation of biogas as metabolic product,
    wherein the purified leaching liquid is fed to an aerobic purification stage to produce an aerobic state, and
    wherein the purified and regenerated leaching liquid is fed back to the reactor.

14. The process as claimed in claim 13, wherein the reactor has a material inlet area and the process further comprises the step of adding activated sludge from an aerobic activation plant to accelerate reaction in the inlet area.

15. The process as claimed in claim 14, wherein the reactor has a material outlet area, and the process further comprises the step of re-circulating a portion of the treated material from the outlet area and adding the portion to the inlet area to accelerate the reaction.

16. An apparatus for carrying out a process for biological treatment of wet organic waste material using a reactor to leach at least one of soluble organic substances, soluble inorganic substances, and water soluble fatty acids, out of the material, the apparatus comprising:

an elongate reactor;

an agitating/circulating/transporting mechanism having a horizontal reversibly rotating shaft;

an inlet port for the material;

an outlet port for the material;

spraying arms for applying leaching liquid in the reactor interior; and chambers provided in a lower part of the reactor said chambers performing at least one of receiving the liquid and feeding fresh air.

17. The apparatus as claimed in claim 16, wherein the agitating/circulating/transporting mechanism comprises paddle shaped or blade shaped circulation elements turnable to select between creating forward and backward motion of the material.

18. The apparatus as claimed in claim 17, wherein the circulation elements are disposed on the shaft in at least one of the following configurations: opposite each other, overlapping each other, and adjacent each other.

19. The apparatus as claimed in claim 17, wherein the circulation elements are axially offset by a predetermined angle, and have at least one of an inclined surface and curved surface.

20. The apparatus as claimed in claim 16, further comprising a transport device to re-circulate treated material to the inlet area.

21. A process for biological treatment of organic waste materials using a solid waste reactor, comprising the steps of:

charging the reactor with the waste material at a first end of the reactor;

feeding air and water to the waste material to cause aerobic degradation of the material, whereby the material heats to a process temperature;

applying a leaching liquid to the waste material so that at least one of soluble organic substances, soluble inorganic substances, and water soluble fatty acids are leached from the waste material and transferred into the leaching liquid;

agitating, circulating and transporting the waste material with an agitating/circulating/transporting mechanism to mix the waste material, prevent the formation of bypass channels in the waste material, and transport the waste material towards a second end of the reactor;

removing the leaching liquid from the lower portion of the reactor;

treating the removed leaching liquid to obtain regenerated leaching liquid;

feeding the regenerated leaching liquid to the reactor for use in the applying step; and removing the material at the second end of the reactor.

* * * * *